(12) United States Patent
Kitahara et al.

(10) Patent No.: US 9,939,433 B2
(45) Date of Patent: Apr. 10, 2018

(54) LATEX PARTICLES FOR MEASURING PARTICLE AGGLUTINATION

(71) Applicant: SEKISUI MEDICAL CO., LTD., Tokyo (JP)

(72) Inventors: Shinichiro Kitahara, Ryugasaki (JP); Yuki Takahashi, Ryugasaki (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 0 days.

(21) Appl. No.: 14/369,439

(22) PCT Filed: Dec. 28, 2012

(86) PCT No.: PCT/JP2012/084175
§ 371 (c)(1),
(2) Date: Jun. 27, 2014

(87) PCT Pub. No.: WO2013/100146
PCT Pub. Date: Jul. 4, 2013

(65) Prior Publication Data
US 2014/0377881 A1    Dec. 25, 2014

(30) Foreign Application Priority Data

Dec. 28, 2011   (JP) ................................ 2011-287791
Feb. 10, 2012   (JP) ................................ 2012-027768

(51) Int. Cl.
*G01N 33/53*     (2006.01)
*G01N 33/543*    (2006.01)
(Continued)

(52) U.S. Cl.
CPC ......... *G01N 33/5306* (2013.01); *C08F 2/30* (2013.01); *C08F 212/08* (2013.01); *C08L 25/18* (2013.01);
(Continued)

(58) Field of Classification Search
CPC .................................................. G01N 33/573
See application file for complete search history.

(56) References Cited

U.S. PATENT DOCUMENTS 4,060,597 A * 11/1977 Sato et al. ..................... 436/534
4,130,526 A * 12/1978 Nakayama ............. C09D 5/024
                                                                524/367
(Continued)

FOREIGN PATENT DOCUMENTS

JP     2000-146974 A     5/2000
JP     2000-355554 A    12/2000
(Continued)

OTHER PUBLICATIONS

Porter et al. "The polyoxyethylene/polyoxypropylene block co-polymer Poloxamer-407 selectively redirects intravenously injected microspheres to sinusoidal endothelial cells of rabbit bone marrow", vol. 305, No. 1, pp. 62-66, published Jun. 1992.*

(Continued)

*Primary Examiner* — Tracy Vivlemore
*Assistant Examiner* — Nam P Nguyen
(74) *Attorney, Agent, or Firm* — Birch, Stewart, Kolasch & Birch, LLP

(57) ABSTRACT

Latex particles for a particle agglutination assay, with which it is possible to carry out high-sensitivity assay while highly suppressing a non-specific reaction are disclosed. The latex particles being obtained by emulsion polymerization with a polymerizable monomer having a phenyl group, and a polymerizable monomer having a phenyl group and a sulfonate in an aqueous medium including a nonionic surfactant at a concentration of 0.005 to 0.02 wt % based on the aqueous medium, the latex particles having an average particle size of 0.005 to 1.0 μm.

11 Claims, 6 Drawing Sheets

(51) Int. Cl.
| | | |
|---|---|---|
| *C08F 212/08* | (2006.01) | |
| *C08F 2/30* | (2006.01) | |
| *C08L 25/18* | (2006.01) | |
| *C08L 71/00* | (2006.01) | |

(52) U.S. Cl.
CPC ........ *C08L 71/00* (2013.01); *G01N 33/54313* (2013.01); *G01N 33/54393* (2013.01)

(56) References Cited

U.S. PATENT DOCUMENTS

| | | | |
|---|---|---|---|
| 5,330,582 A * | 7/1994 | Chihara et al. | ............ 134/40 |
| 7,867,785 B2 | 1/2011 | Obana | |
| 2004/0171176 A1 | 9/2004 | Obana | |
| 2008/0113452 A1 | 5/2008 | Obana | |
| 2008/0207774 A1 | 8/2008 | Krishnan | |
| 2014/0080143 A1* | 3/2014 | Takahashi et al. | ............ 435/7.4 |

FOREIGN PATENT DOCUMENTS

| | | | |
|---|---|---|---|
| JP | | 3708942 B2 | 10/2005 |
| WO | WO 03/005031 A1 | | 1/2003 |

OTHER PUBLICATIONS

Berthod et al. ("Polyoxyethylene alkyl ether nonionic surfactants: physicochemical properties and use for cholesterol determination in food", Talanta, vol. 55 (2001) pp. 69-83.*

Kabanov et al., "Pluronic bock copolymers: novel functional molecules for gene therapy", Advanced Drug Delivery Reviews, vol. 54 (2002) pp. 223-233.*

International Search Report issued in PCT/JP2012/084175, dated Apr. 16, 2013.

Extended European Search Report dated Jul. 14, 2015, for European Application No. 12863363.3.

* cited by examiner

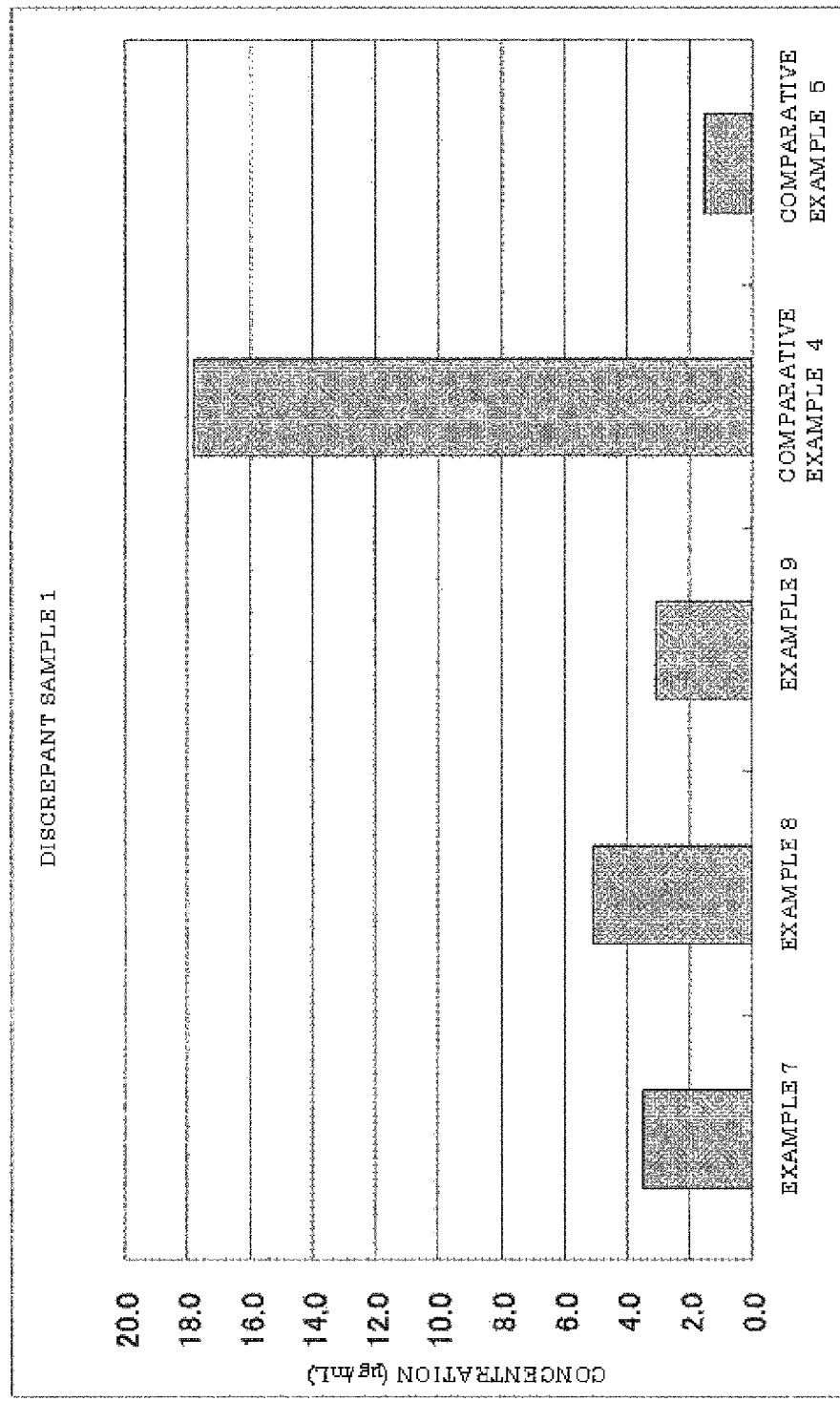

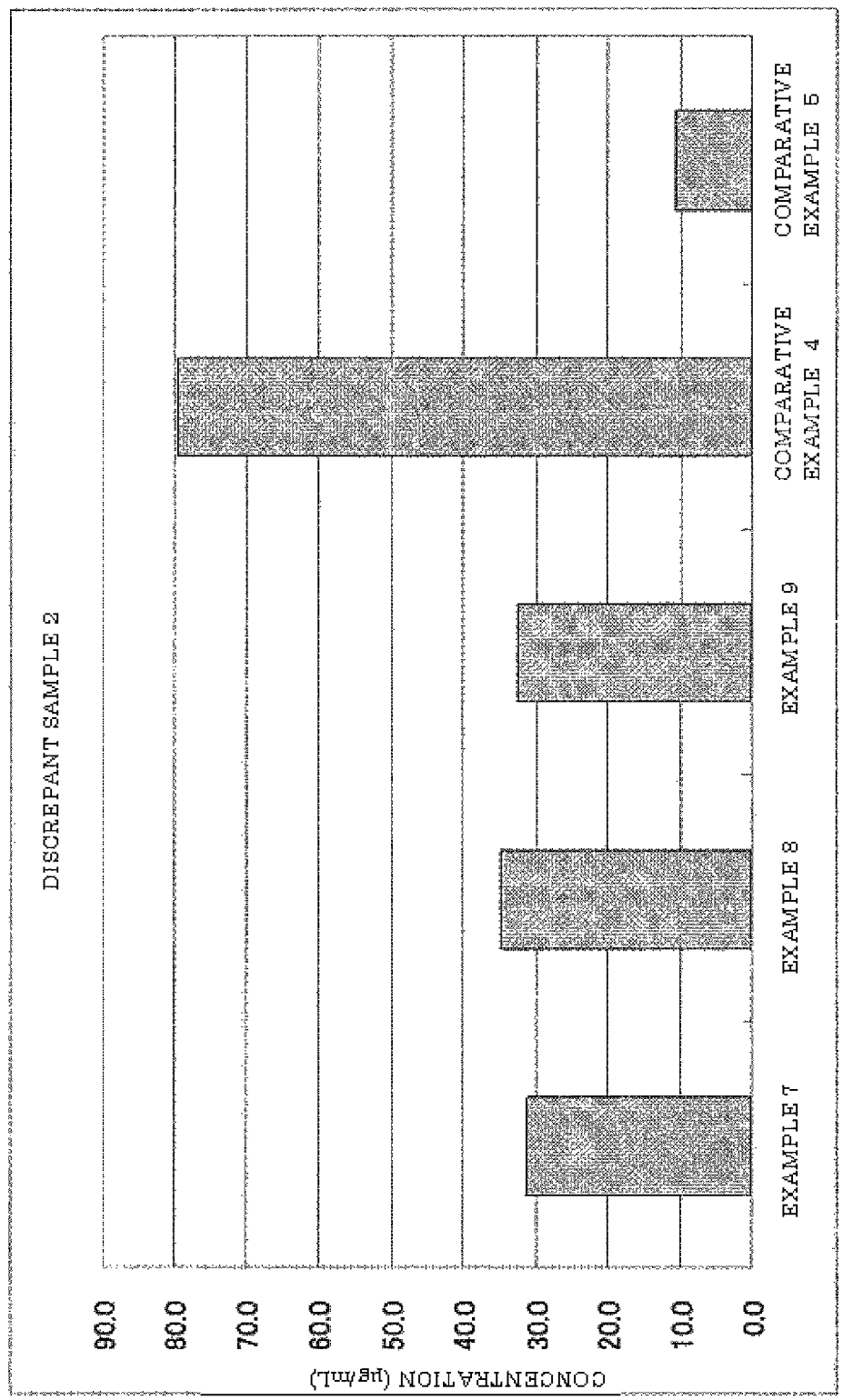

LATEX PARTICLES FOR MEASURING PARTICLE AGGLUTINATION

TECHNICAL FIELD

The invention relates to latex particles for a particle agglutination assay that can implement a high-sensitivity assay while highly suppressing a non-specific reaction, and a particle agglutination assay reagent that utilizes the latex particles.

BACKGROUND ART

In the field of clinical examination, an immunoassay that utilizes an antigen-antibody reaction has been widely used to quantitatively determine a trace substance in the sample. In particular, latex immunoturbidimetric method that utilizes latex particles that support an antibody or the like (hereinafter may be referred to as "sensitized latex particles") has been widely used in clinical laboratories and the like since the operation is easy, and only a short measurement time is required. When using latex immunoturbidimetric method, an antigen or an antibody in the sample is quantitatively determined by optically detecting a change in absorbance due to agglutination of the sensitized latex particles caused by formation of an immune complex between the antigen and the antibody. Such a change in absorbance is based on an apparent change in particle size due to agglutination of the sensitized latex particles.

Polystyrene-based latex particles that include polystyrene as the main component have been used for latex immunoturbidimetry since the polystyrene-based latex particles allow easy immobilization of an antigen or an antibody that specifically reacts with the detection target substance (in other words, it is easy to sensitize the latex particles), are relatively inexpensive, and allow easily control of a polymerization reaction (see Patent Document 1). However, the latex particles that include polystyrene as the main component, which have an advantage in that an antigen or an antibody can be physically adsorbed on the latex particles (in other words, the latex particles can be sensitized through physical adsorption) may cause agglutination of the sensitized latex particles that is not based on a specific reaction due to an antigen-antibody reaction, (i.e., non-specific reaction) due to their property of allowing non-detection target proteins or the like in the sample adsorbed thereon. Therefore, it has been desired to suppress such a non-specific reaction.

A technique has been known that blocks the latex particles sensitized with an antigen or an antibody with bovine serum albumin (BSA) or the like in order to suppress a non-specific reaction. However, a non-specific reaction may not be sufficiently suppressed by such a technique, and a high background value may be obtained. Therefore, suppression of a non-specific reaction has been a major challenge in preparing a reagent that can implement a high-sensitivity assay.

In Patent Document 2, a nonionic surfactant is added to the blocking buffer when sensitizing the latex particles with an antigen or an antibody, and a nonionic surfactant is added to the assay reagent in order to suppress a non-specific reaction. However, since the nonionic surfactant is present on the surface of the particles, and is also included in the assay reagent, a decrease in sensitivity may occur due to inhibition of an immune reaction, for example. Therefore, development of a method that suppresses a non-specific reaction by improving the latex particles has been desired.

Patent Document 3 discloses latex particles produced by emulsion polymerization that utilizes a nonionic surfactant or an anionic surfactant as an emulsifier, which the latex particles per se are designed to suppress a non-specific reaction, and can be easily produced. However, since the emulsifier is used at a concentration of 0.05 wt % or more based on the aqueous medium when producing the latex particles of Patent Document 3, a sufficient sensitivity may not be achieved using the obtained latex particles due to the effects of the residual emulsifier.

RELATED-ART DOCUMENT

Patent Document

Patent Document 1: Japanese Patent No. 3708942
Patent Document 2: JP-A-2000-146974
Patent Document 3: JP-A-2000-355554

SUMMARY OF THE INVENTION

Technical Problem

An object of the invention is to easily produce latex particles for a particle agglutination assay that can implement a high-sensitivity assay while sufficiently suppressing a non-specific reaction, and a particle agglutination assay reagent that utilizes the latex particles.

The inventors of the invention conducted extensive studies in order to achieve the above object, and succeeded in producing latex particles for a particle agglutination assay according to the invention. Specifically, the invention provides the following.

[1] Latex particles for a particle agglutination assay, wherein the latex particles being obtained by emulsion polymerization with a polymerizable monomer having a phenyl group, and a polymerizable monomer having a phenyl group and a sulfonate; the emulsion polymerization is performed in an aqueous medium including a nonionic surfactant at a concentration of 0.005 to 0.02 wt % based on the aqueous medium; the latex particles having an average particle size of 0.005 to 1.0 μm.

[2] The latex particles according to [1], wherein the nonionic surfactant is one or more of polyoxyethylene-polyoxypropylene block copolymer or one or more of polyoxyalkylene alkyl ether.

[3] The latex particles according to [2], wherein the polyoxyethylene-polyoxypropylene block copolymer has a structure represented by the following formula (I), and has a weight average molecular weight of 1000 to 15,000 and an EO content of 5 to 90%,

$$\mathrm{HO(C_2H_4O)}_a\mathrm{-(C_3H_6O)}_b\mathrm{-(C_2H_4O)}_c\mathrm{H} \quad (I)$$

wherein a, b, and c are arbitrary integers, a+c being determined so that oxyethylene has an average degree of polymerization of 2 to 270, and b being determined so that oxypropylene has an average degree of polymerization of 15 to 40, provided that a+b+c is 17 to 300.

[4] The latex particles according to [3], wherein the polyoxyethylene-polyoxypropylene block copolymer is selected from the group consisting of
(1) a polyoxyethylene-polyoxypropylene block copolymer having a weight average molecular weight of 1333 and an EO content of 10%,
(2) a polyoxyethylene-polyoxypropylene block copolymer having a weight average molecular weight of 2222 and an EO content of 10%, (3) a polyoxyethylene-polyoxypropylene block copolymer having a weight average molecular weight of 8000 and an EO content of 85%, and
(4) a polyoxyethylene-polyoxypropylene block copolymer having a weight average molecular weight of 13,333 and an EO content of 85%.
[5] The latex particles according to [2], wherein the polyoxyalkylene alkyl ether has a structure represented by the following formula (II), and has an HLB value of 5.0 to 19.3, $$R^1O(AO)_n\text{—}H \quad (II)$$

wherein $R^1$ is an alkyl group or an alkenyl group having 8 to 22 carbon atoms, AO is an oxyalkylene group, A is an alkyl group having 2 to 4 carbon atoms, and n is an integer from 2 to 15, n being the average addition molar number of the oxyalkylene group represented by AO.
[6] The latex particles according to [2], wherein the polyoxyalkylene alkyl ether is selected from the group consisting of (1) polyoxyethylene tridecyl ether (HLB: 10.5), (2) polyoxyethylene lauryl ether (HLB: 9.5), and (3) polyoxyethylene 2-ethylhexyl ether (HLB: 14.6).
[7] The latex particles according to [2], wherein the polymerizable monomer having a phenyl group is styrene, and a polymerizable monomer having a phenyl group and a sulfonate is sodium styrenesulfonate.
[8] A particle agglutination assay reagent including the latex particles according to any one of [1] to [7].
[9] A particle agglutination assay reagent including the latex particles according to any one of [1] to [7], the latex particles supporting an antigen or an antibody through physical adsorption.

Advantageous Effects of the Invention

Since non-detection target proteins or the like in the sample that causes a non-specific agglutination reaction are prevented from being adsorbed on the latex particles by the use of latex particles for particle agglutination assay and particle agglutination assay reagents according to the invention, and only the desired specific agglutination reaction occurs, it is possible to obtain a particle agglutination assay reagent that can achieve higher sensitivity as compared with a known particle agglutination assay reagent.

Since the latex particles can be produced by a single-step polymerization reaction, the latex particles can be obtained in a very simple way. Since the latex particles are designed so that immobilization of (sensitization with) an antigen or an antibody is achieved through physical adsorption, it is possible to easily produce a particle agglutination assay reagent that can achieve high sensitivity.

BRIEF DESCRIPTION OF DRAWINGS

FIG. 5 illustrates a graph when an assay was performed on the D-dimer discrepant sample 1 (RF08FD1832) using the latex particles of Examples 7 to 9 and Comparative Examples 4 and 5 that were sensitized with the anti-D-dimer antibody, and the concentration was calculated based on the calibration curve (see FIG. 4).
FIG. 6 illustrates a graph when an assay was performed on the D-dimer discrepant sample 2 (RF08FD1836) using the latex particles of Examples 7 to 9 and Comparative Examples 4 and 5 that were sensitized with the anti-D-dimer antibody, and the concentration was calculated based on the calibration curve (see FIG. 4).

DESCRIPTION OF EMBODIMENTS

Figure 1:
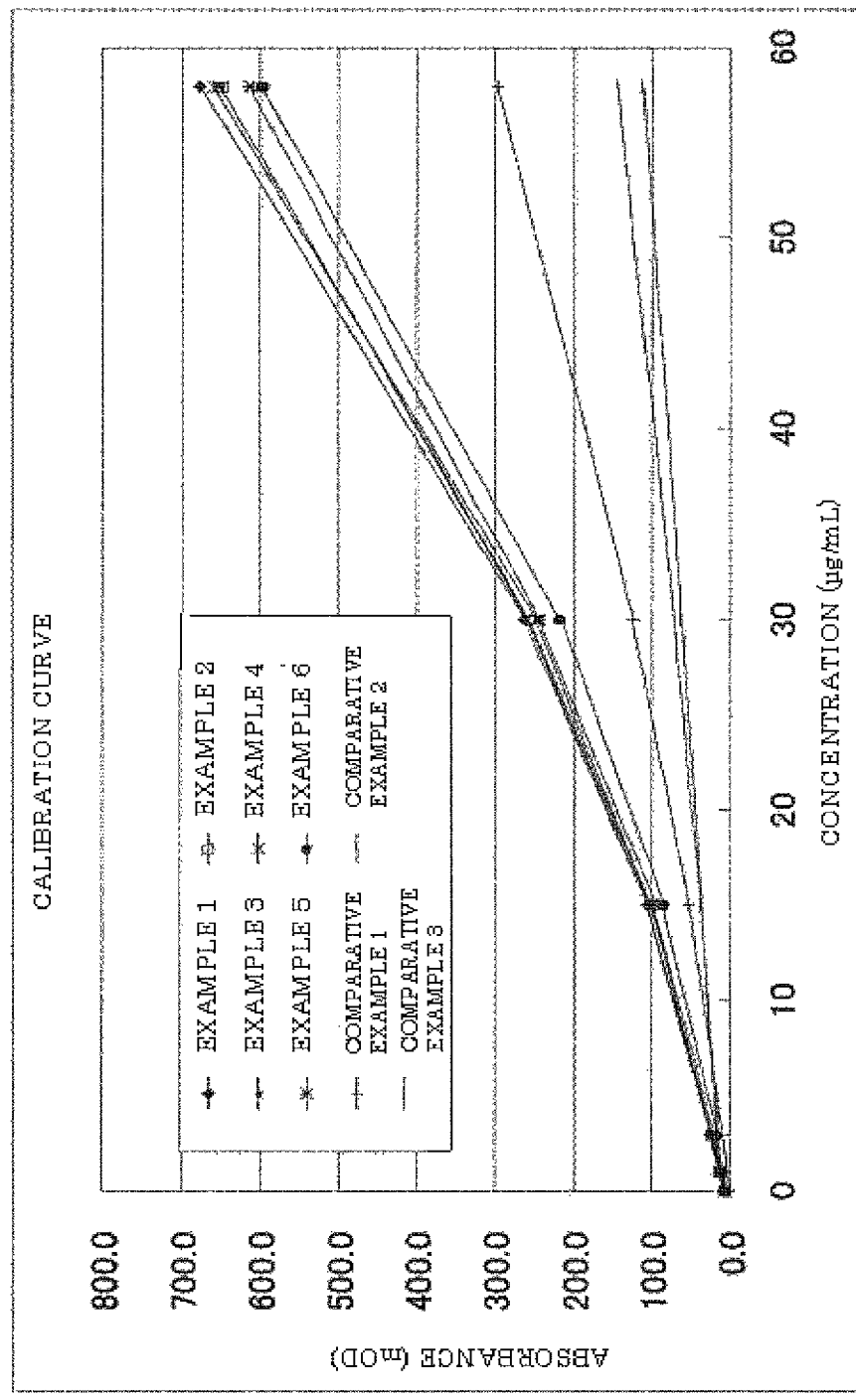
FIG. 1 illustrates a calibration curve drawn when an assay was performed on the standard D-dimer antigen using the latex particles of Examples 1 to 6 and Comparative Examples 1 to 3 that were sensitized with (immobilizing thereon) the anti-D-dimer antibody.

The invention is described in detail below. The polymerizable monomer that has a phenyl group is not particularly limited. Examples of the polymerizable monomer that has a phenyl group include styrene, o-methylstyrene, p-methylstyrene, p-chlorostyrene, 4-vinylbenzoic acid, and the like. These polymerizable monomers may be used either alone or in combination. Among these, styrene is preferably used as the polymerizable monomer that has a phenyl group.

The polymerizable monomer that has a phenyl group and a sulfonate is not particularly limited as long as the polymerizable monomer is a monomer that allows a sulfonic acid group to be present on the surface of the resulting latex particles. Examples of the polymerizable monomer that has a phenyl group and a sulfonate include a styrenesulfonate, a divinylbenzenesulfonate, an o-methylstyrenesulfonate, a p-methylstyrenesulfonate, and the like. The polymerizable monomer that has a phenyl group and a sulfonate may be a sodium salt, a potassium salt, a lithium salt, an ammonium salt, or the like. These polymerizable monomers may be used either alone or in combination. It is preferable to use a styrenesulfonate, and more preferably sodium styrenesulfonate as the polymerizable monomer that has a phenyl group and a sulfonate.

The latex particles are obtained by emulsion polymerizing the polymerizable monomer that has a phenyl group, and the polymerizable monomer that has a phenyl group and a sulfonate in an aqueous medium that includes the nonionic surfactant at a concentration of 0.005 to 0.02 wt % based on the aqueous medium. The term "emulsion polymerization" used herein excludes a "soap-free polymerization method" that does not add a surfactant (emulsifier) to the reaction system when effecting polymerization, and refers to any polymerization method that effects polymerization in a state in which a small amount (i.e., in the above concentration range) of surfactant is added to the aqueous medium. The surfactant used in connection with the invention need not necessarily emulsify the component subjected to polymerization, differing from a conventional case where the surfactant is used as an emulsifier. The surfactant may or may not emulsify the component subjected to polymerization.

Emulsion polymerization may be effected using a known method. For example, the polymerizable monomer that has a phenyl group, the polymerizable monomer that has a phenyl group and a sulfonate, and an initiator may be added to a reaction vessel that is charged with the aqueous medium that includes the nonionic surfactant at a concentration of 0.005 to 0.02 wt % based on the aqueous medium, and the mixture may be heated with stirring in a nitrogen atmosphere. In this case, the polymerization temperature is preferably 50 to 100° C., and more preferably 60 to 85° C. The polymerization time is determined depending on the composition of each polymerizable monomer, the concentration of each polymerizable monomer, the type of initiator, and the like, but is normally 5 to 50 hours.

The aqueous medium is preferably water (deionized water) alone, or a mixed solvent of water and a water-soluble solvent such as an alcohol that is miscible with water (e.g., a mixed solvent of water and an alcohol (e.g., ethanol)). It is more preferable to use water alone as the aqueous medium.

A known nonionic surfactant may be used as the nonionic surfactant that is dissolved in the aqueous medium. Examples of the preferable nonionic surfactant may be classified into the following large groups: polyoxyethylene-polyoxypropylene block copolymers and polyoxyalkylene alkyl ethers.

The polyoxyethylene-polyoxypropylene block copolymer has a structure represented by the following formula (I), and has a weight average molecular weight of 1000 to 15,000 and an EO content of 5 to 90%.

$$HO(C_2H_4O)_a—(C_3H_6O)_b—(C_2H_4O)_cH \quad (I)$$

wherein a, b, and c are arbitrary integers, a+c being determined so that oxyethylene has an average degree of polymerization of 2 to 270, and b being determined so that oxypropylene has an average degree of polymerization of 15 to 40, provided that a+b+c is 17 to 300.

The polyoxyethylene-polyoxypropylene block copolymer has a structure in which a hydrophobic polyoxypropylene block polymer is situated between two hydrophilic polyoxyethylene block polymers (see above), and functions as a nonionic surfactant.

Examples of a commercially available product containing of the polyoxyethylene-polyoxypropylene block copolymer include the nonionic surfactants available under the registered trademark "Epan" (manufactured by Dai-ichi Kogyo Seiyaku Co., Ltd.), and the nonionic surfactants available under the registered trademark "Pluronic" (manufactured by ADEKA CORPORATION).

Note that the components of different commercially available products an identical polyoxyethylene-polyoxypropylene block copolymer may not completely coincide with each other. It is considered that a person having ordinary skill in the art would necessarily understand that such a case is specific to a polymer.

Specific examples of a commercially available product of the polyoxyethylene-polyoxypropylene block copolymer are given below.

Specific examples of the nonionic surfactants available under the registered trademark "Epan" (manufactured by Dai-ichi Kogyo Seiyaku Co., Ltd.) include the following.
Epan 410: weight average molecular weight: 1333, EO content: 10%
Epan 710: weight average molecular weight: 2222, EO content: 10%
Epan 485: weight average molecular weight: 8000, EO content: 85%
Epan 785: weight average molecular weight: 13,333, EO content: 85%
Epan 750: weight average molecular weight: 4000, EO content: 50%
Epan 420: weight average molecular weight: 1500, EO content: 20%
Epan 450: weight average molecular weight: 2400, EO content: 50%
Epan 610: weight average molecular weight: 2000, EO content: 10%
Epan 680: weight average molecular weight: 8800, EO content: 80%
Epan 740: weight average molecular weight: 3300, EO content: 40%
Epan 720: weight average molecular weight: 2500, EO content: 20%

Among these, Epan 410, Epan 710, Epan 485, and Epan 785 are preferable.

Specific examples of the nonionic surfactants available under the registered trademark "Pluronic" (manufactured by ADEKA CORPORATION) include the following. Note that PPG refers to polypropylene glycol (synonymous with polyoxypropylene).
Pluronic L-42: PPG molecular weight: 1200, EO content: 20%
Pluronic L-43: PPG molecular weight: 1200, EO content: 30%
Pluronic L-44: PPG molecular weight: 1200, EO content: 40%
Pluronic L-61: PPG molecular weight: 1750, EO content: 10%
Pluronic L-62: PPG molecular weight: 1750, EO content: 20%
Pluronic L-64: PPG molecular weight: 1750, EO content: 40%
Pluronic P-65: PPG molecular weight: 1750, EO content: 50%
Pluronic F-68: PPG molecular weight: 1750, EO content: 80%

The polyoxyalkylene alkyl ether has a structure represented by the following formula (II), and has an HLB value of 5.0 to 19.3.

$$R^1O(AO)_n—H \quad (II)$$

wherein $R^1$ is an alkyl group or an alkenyl group having 8 to 22 carbon atoms, AO is an oxyalkylene group, A is an alkyl group having 2 to 4 carbon atoms, and n is an integer from 2 to 15, n being the average additional molar number of the oxyalkylene group represented by AO.

Specific examples of the alkyl group or alkenyl group having 8 to 22 carbon atoms represented by $R^1$ include an octyl group (number of carbon atoms: 8), a 2-ethylhexyl group (number of carbon atoms: 8), a decyl group (number of carbon atoms: 10), an isodecyl group (number of carbon atoms: 10), a lauryl (dodecyl) group (number of carbon atoms: 12), a tridecyl group (number of carbon atoms: 13), a cetyl group (number of carbon atoms: 16), an octadecyl group (number of carbon atoms: 18), an oleyl group (number of carbon atoms: 18), and the like. The alkyl group or alkenyl group having 8 to 22 carbon atoms represented by $R^1$ may be either linear or branched, and may include one or more unsaturated bonds.

Specific examples of the oxyalkylene group having 2 to 4 carbon atoms represented by AO include an oxyethylene group, an oxypropylene group, and an oxybutylene group. The oxyalkylene group may be linear or branched.

Specific examples of the polyoxyalkylene alkyl ether and a commercially available product thereof include polyoxyethylene 2-ethylhexyl ether (e.g., "Newcol 1008" manufactured by Nippon Nyukazai Co., Ltd.), a polyoxyalkylene branched decyl ether (e.g., "Noigen XL" (wherein the polyoxyalkylene moiety consists of a polymer of a short-chain polyoxyalkylene and polyoxyethylene) manufactured by Dai-ichi Kogyo Seiyaku Co., Ltd.), polyoxyethylene isodecyl ether (e.g., "Noigen SD" manufactured by Dai-ichi Kogyo Seiyaku Co., Ltd.), polyoxyethylene lauryl ether (e.g., "DKSNL" manufactured by Dai-ichi Kogyo Seiyaku Co., Ltd.), polyoxyethylene tridecyl ether (e.g., "Noigen TDS" manufactured by Dai-ichi Kogyo Seiyaku Co., Ltd.), a polyoxyalkylene tridecyl ether (e.g., "Noigen TDX" (wherein the polyoxyalkylene moiety consists of a polymer of polyoxypropylene and polyoxyethylene) manufactured by Dai-ichi Kogyo Seiyaku Co., Ltd.), a polyoxyalkylene alkyl ether (e.g., "Noigen LF" manufactured by Dai-ichi Kogyo Seiyaku Co., Ltd.), polyoxyethylene cetyl ether (e.g., "Newcol 1606" manufactured by Nippon Nyukazai Co., Ltd.), polyoxyethylene oleyl ether (e.g., "Newcol 1204" manufactured by Nippon Nyukazai Co., Ltd.), and the like.

Among these, Noigen TDS-50 (polyoxyethylene tridecyl ether, HLB: 10.5), DKSNL 40 (polyoxyethylene lauryl ether, HLB: 9.5), and Newcol 1008 (polyoxyethylene 2-ethylhexyl ether, HLB: 14.6) are preferable.

The HLB value may be calculated by Griffin's method using the following formula (III).

$$HLB \text{ value} = 20 \times \text{sum of formula weight of hydrophilic portion/molecular weight} \quad (III)$$

The HLB value is information useful for specifying the structure of the polyoxyalkylene alkyl ether. For example, the number of moles (n) of polyoxyethylene of Noigen TDS-50 (polyoxyethylene tridecyl ether, HLB: 10.5) can be estimated to be about 5 using the HLB value (=sum of formula weight of polyoxyethylene/(molecular weight of tridecyl ether portion+sum of formula weight of polyoxyethylene) (i.e., $10.5=(44n)/(199+44n)$).

The nonionic surfactants are used at a concentration of 0.005 to 0.02 wt % based on the aqueous medium. If the concentration of the nonionic surfactant is less than 0.005 wt %, the effects of the nonionic surfactant may be insufficient. If the concentration of the nonionic surfactant exceeds 0.02 wt %, a non-specific reaction is suppressed, but a substance (antigen or antibody) that specifically reacts with the detection target substance may be physically adsorbed on the surface of the particles to only a small extent. As a result, a deterioration in sensitivity may occur. The above nonionic surfactants may be used either alone or in combination. When mixing two or more nonionic surfactants, the total concentration of the two or more nonionic surfactants is adjusted to 0.005 to 0.02 wt %.

A known radical initiator may be used as the initiator. Examples of the radical initiator include persulfates such as potassium persulfate, sodium persulfate, and ammonium persulfate, azo compounds such as 2,2'-azobisisobutyronitrile, 2,2'-azobis(4-methoxy-2,4-dimethylvaleronitrile), and 2,2'-azobis-2,4-dimethylvaleronitrile, and organic peroxides such as benzoyl peroxide, di-t-butyl peroxide, lauroyl peroxide, and t-butyl peroxy-2-ethylhexanoate. It is preferable to use a persulfate, and more preferably potassium persulfate. The initiator may be used in an arbitrary amount. The initiator is normally used in a ratio of 0.01 to 5 wt % based on the amount of the polymerizable monomers.

A polymerizable unsaturated monomer may be polymerized together with the above polymerizable monomers depending on the application of the latex particles. The polymerizable unsaturated monomer is not particularly limited as long as the polymerizable unsaturated monomer can be used for normal radical polymerization. Examples of the polymerizable unsaturated monomer include (meth)acrylic acid, (meth)acrylates, styrene derivatives, (meth)acrylonitrile, (meth)acrylic amides, vinyl halides, vinyl esters, (meth)acrolein, maleic acid derivatives, fumaric acid derivatives, and the like. Note that the term "(meth) acrylic acid" used herein refers to acrylic acid or methacrylic acid.

The average particle size of the latex particles is 0.005 to 1.0 µm. If the average particle size of the latex particles is less than 0.005 µm, the amount of optical change due to agglutination of the latex particles may be too small, and sensitivity necessary for the assay may not be obtained. Moreover, centrifugation may take time when preparing a reagent, and the reagent cost may increase. If the average particle size of the latex particles exceeds 1.0 µm, the amount of optical change due to agglutination of the latex particles may exceed the allowable range for detection when the concentration of the test substance is high, and an amount of optical change corresponding to the amount of the test substance may not be obtained. The average particle size of the latex particles is preferably 0.05 to 0.7 µm, and more preferably 0.05 to 0.4 µm, although the preferable range may differ depending on a measurement method and a measurement system that utilize the latex particles.

The coefficient of variation (CV value) in the particle size of the latex particles is preferably 20% or less. If the coefficient of variation (CV value) in the particle size of the latex particles exceeds 20%, the reproducibility of the assay reagent may deteriorate due to a deterioration in lot-to-lot reproducibility. The coefficient of variation (CV value) in the particle size of the latex particles is more preferably 15% or less. Note that the coefficient of variation (CV value) in the particle size of the latex particles is calculated using the following expression.

$$\text{Coefficient of variation (CV value) in particle size} = \text{standard deviation of particle size/average particle size}$$

The latex particles are obtained in a state in which the latex particles are suspended in the aqueous medium (e.g., water). The concentration of the latex particles is not particularly limited, but is preferably 1 to 20 wt %. If the concentration of the latex particles is less than 1 wt %, it is necessary to perform a concentration operation when preparing a reagent. If the concentration of the latex particles exceeds 20 wt %, agglutination may occur.

The latex particles that support a substance that specifically reacts with the detection target substance through physical adsorption (sensitized latex particles), and the particle agglutination assay reagent that includes the latex particles are also included within the scope of the invention. The substance that specifically reacts with the detection target substance is not particularly limited as long as it is a physiologically active substance that is normally used as an immunoserological assay reagent (i.e., a reagent used for immunoagglutination and agglutination inhibition) or a biochemical assay reagent. It is preferable to use a substance that can be used for an antigen-antibody reaction.

Examples of the substance that can be used for an antigen-antibody reaction include antigens and antibodies such as proteins, nucleic acid, nucleoproteins, estrogen, and lipids. Examples of the antigens include antigens, receptors, enzymes, and the like. Specific examples of the antigens include β2-microglobulin, C-reactive protein (CRP), insulin, human fibrinogen, ferritin, rheumatoid factor (RF), α-fetoprotein (AFP), *mycoplasma* antigen, HBs antigen, and the like. Examples of the antibodies include antibodies to toxins, pathogenic bacteria, and the like. Specific examples of the antibodies include anti-streptolysin O antibody, antiestrogen antibody, anti-β2-microglobulin antibody, anti-*Treponema pallidum* antibody, an antibody to syphilis lipid antigen, anti-HBs antibody, anti-HBc antibody, anti-HBe antibody, anti-PSA antibody, anti-CRP antibody, anti-insulin antibody, anti-D-dimer antibody, and the like. The antibody may be an immunoglobulin molecule, or may be a fragment (e.g., F(ab')2). A polyclonal antibody or a monoclonal antibody may be used as the antibody.

The latex particles may be caused to support the substance that specifically reacts with the detection target substance (may be undergo sensitization) using an arbitrary known method as long as the substance is supported on the latex particles through physical adsorption.

The latex particles after supported the substance may optionally be blocked using bovine serum albumin or the like, and dispersed in an appropriate buffer to prepare a sensitized latex dispersion. The sensitized latex dispersion may be combined with a buffer, a standard substance, and the like used for the assay to provide a particle agglutination assay reagent (kit).

The amount of the substance that specifically reacts with the detection target substance, and which is supported on the latex particles, is determined depending on the type of substance that specifically reacts with the detection target substance (test substance).

A sensitizer may be added to the assay reagent that includes the latex particles that support an antigen, an antibody, or the like in order to improve sensitivity, or promote an antigen-antibody reaction. Examples of the sensitizer include alkylated polysaccharides such as methyl cellulose and ethyl cellulose, pullulan, polyvinylpyrrolidone, and the like.

A non-specific reaction is highly suppressed by utilizing the latex particles according to the invention. In order to further suppress a non-specific reaction due to another substance present in the sample, or improve the storage stability of the reagent, a component known in the field of immunoassay and reagents that utilize latex particles (e.g., a protein such as albumin (bovine serum albumin or egg albumin), casein, or gelatin, a degradation product thereof, a peptide, an amino acid, or a surfactant) may be added to the reagent.

The detection target substance may be diluted with an appropriate diluent. An appropriate buffer having a pH of 5.0 to 9.0 may be used as the diluent. Examples of such a buffer include a phosphate buffer, a glycine buffer, a Tris buffer, a borate buffer, a citrate buffer, and the like.

According to the assay reagent that includes the latex particles according to the invention that support an antigen, an antibody, or the like, the degree of reaction of the detection target substance in the sample can be determined by optically measuring the degree of agglutination of the latex particles that occurs due to reactions between the detection target substance in the sample and the substance that is supported on the latex particles and specifically reacts with the detection target substance. The optical measurement may be performed using a normal automatic biochemical analyzer such as an optical device that can detect the intensity of scattered light, the intensity of transmitted light, the absorbance, or the like, and an optical device that implements a plurality of detection methods.

The degree of agglutination of the latex particles may be optically measured using a known method. Examples of such a method include a turbidimetric method that determines the formation of agglutination based on an increase in turbidity, a method that determines the degree of agglutination based on a change in particle size distribution or average particle size, an integrating sphere nephelometric method that determines a change in forward scattered light due to agglutination using an integrating sphere, and compares the ratio with respect to the intensity of transmitted light, and the like.

A change in the degree of agglutination may be determined by a rate assay that obtains at least two measured values at different time points, and determines the degree of agglutination based on an increase (increase rate) in the measured values, an end point assay that obtains one measured value at a certain time point (normally a time point considered to be the end point of the reaction), and determines the degree of agglutination based on the measured value, or the like. It is preferable to use the end point assay by turbidimetry from the viewpoint of convenience and promptness.

EXAMPLES

The invention is further described below by way of examples. The particle size of the latex particles was measured as described below.

Measurement of Particle Size of Latex Particles

The latex particles were placed on a collodion film using a normal method. An image of the latex particles was captured using a transmission electron microscope, and the particle size of the latex particles (100 or more particles) within the image was measured to calculate the average particle size and the standard deviation.

Example 1

A glass reaction vessel (volume: 2 L) equipped with a stirrer, a reflux condenser, a temperature detector, a nitrogen inlet tube, and a jacket was charged with a solution prepared by dissolving 0.10 g of a polyoxyethylene-polyoxypropylene block copolymer ("Epan 410" manufactured by Dai-ichi Kogyo Seiyaku Co., Ltd., molecular weight: 1333, EO content: 10%) in 1000 g of ultrapure water, 150 g of a styrene monomer, 0.80 g of sodium styrenesulfonate, and 0.72 g of potassium persulfate. After replacing the atmosphere inside the vessel with nitrogen gas, the monomers were polymerized at 70° C. for 24 hours with stirring (210 rpm).

After completion of polymerization, the solution was filtered through a filter paper to obtain latex particles. The latex particles were subjected to dialysis for 48 hours using a dialysis membrane to obtain purified latex particles. The latex particles had a particle size of 0.114 μm (CV: 10.4%).

Example 2

Latex particles were obtained in the same manner as in Example 1, except that 0.10 g of Epan 710 (manufactured by Dai-ichi Kogyo Seiyaku Co., Ltd., molecular weight: 2222, EO content: 10%) was used as the polyoxyethylene-polyoxypropylene block copolymer instead of 0.10 g of Epan 410 (manufactured by Dai-ichi Kogyo Seiyaku Co., Ltd.). The latex particles had a particle size of 0.116 μm (CV: 9.6%).

Example 3

Latex particles were obtained in the same manner as in Example 1, except that 0.10 g of Epan 485 (manufactured by Dai-ichi Kogyo Seiyaku Co., Ltd., molecular weight: 8000, EO content: 85%) was used as the polyoxyethylene-polyoxypropylene block copolymer instead of 0.10 g of Epan 410 (manufactured by Dai-ichi Kogyo Seiyaku Co., Ltd.), and the amount of sodium styrenesulfonate was changed from 0.80 g to 2.00 g. The latex particles had a particle size of 0.093 µm (CV: 9.5%).

Example 4

Latex particles were obtained in the same manner as in Example 1, except that 0.10 g of Epan 785 (manufactured by Dai-ichi Kogyo Seiyaku Co., Ltd., molecular weight: 13,333, EO content: 85%) was used as the polyoxyethylene-polyoxypropylene block copolymer instead of 0.10 g of Epan 410 (manufactured by Dai-ichi Kogyo Seiyaku Co., Ltd.), and the amount of sodium styrenesulfonate was changed from 0.80 g to 2.00 g. The latex particles had a particle size of 0.108 µm (CV: 6.6%).

Example 5

Latex particles were obtained in the same manner as in Example 1, except that the amount of the polyoxyethylene-polyoxypropylene block copolymer ("Epan 410" manufactured by Dai-ichi Kogyo Seiyaku Co., Ltd.) was changed from 0.10 g to 0.05 g. The latex particles had a particle size of 0.110 µm (CV: 10.9%).

Example 6

Latex particles were obtained in the same manner as in Example 1, except that the amount of the polyoxyethylene-polyoxypropylene block copolymer ("Epan 410" manufactured by Dai-ichi Kogyo Seiyaku Co., Ltd.) was changed from 0.10 g to 0.20 g. The latex particles had a particle size of 0.104 µm (CV: 11.2%).

Example 7

Latex particles were obtained in the same manner as in Example 1, except that 0.10 g of polyoxyethylene tridecyl ether ("Noigen TDS-50" manufactured by Dai-ichi Kogyo Seiyaku Co., Ltd., HLB: 10.5) (polyoxyalkylene alkyl ether) was used instead of 0.10 g of the polyoxyethylene-polyoxypropylene block copolymer ("Epan 410" manufactured by Dai-ichi Kogyo Seiyaku Co., Ltd.). The latex particles had a particle size of 0.101 µm (CV: 10.2%).

Example 8

Latex particles were obtained in the same manner as in Example 1, except that 0.10 g of polyoxyethylene lauryl ether ("DKSNL-40" manufactured by Dai-ichi Kogyo Seiyaku Co., Ltd., HLB: 9.5) (polyoxyalkylene alkyl ether) was used instead of 0.10 g of the polyoxyethylene-polyoxypropylene block copolymer ("Epan 410" manufactured by Dai-ichi Kogyo Seiyaku Co., Ltd.). The latex particles had a particle size of 0.102 µm (CV: 10.5%).

Example 9

Latex particles were obtained in the same manner as in Example 1, except that 0.10 g of polyoxyethylene 2-ethylhexyl ether ("Newcol 1008" manufactured by Nippon Nyukazai Co., Ltd., HLB: 14.6) was used instead of 0.10 g of the polyoxyethylene-polyoxypropylene block copolymer ("Epan 410" manufactured by Dai-ichi Kogyo Seiyaku Co., Ltd.). The latex particles had a particle size of 0.107 µm (CV: 11.1%).

Comparative Example 1

Latex particles were obtained in the same manner as in Example 1, except that the polyoxyethylene-polyoxypropylene block copolymer ("Epan 410" manufactured by Dai-ichi Kogyo Seiyaku Co., Ltd.) was not used. The latex particles had a particle size of 0.099 µm (CV: 11.1%).

Comparative Example 2

Latex particles were obtained in the same manner as in Example 1, except that the amount of the polyoxyethylene-polyoxypropylene block copolymer ("Epan 410" manufactured by Dai-ichi Kogyo Seiyaku Co., Ltd.) was changed from 0.10 g to 1.00 g. The latex particles had a particle size of 0.105 µm (CV: 9.8%).

Comparative Example 3

Latex particles were obtained in the same manner as in Example 1, except that 1.00 g of Epan 710 (manufactured by Dai-ichi Kogyo Seiyaku Co., Ltd.) was used as the polyoxyethylene-polyoxypropylene block copolymer instead of Epan 410 (manufactured by Dai-ichi Kogyo Seiyaku Co., Ltd.). The latex particles had a particle size of 0.107 µm (CV: 8.6%).

Comparative Example 4

Latex particles were obtained in the same manner as in Example 1, except that the amount of the polyoxyethylene-polyoxypropylene block copolymer ("Epan 410" manufactured by Dai-ichi Kogyo Seiyaku Co., Ltd.) was changed from 0.10 g to 0.04 g. The latex particles had a particle size of 0.102 µm (CV: 9.9%).

Comparative Example 5

Latex particles were obtained in the same manner as in Example 1, except that the amount of the polyoxyethylene-polyoxypropylene block copolymer ("Epan 410" manufactured by Dai-ichi Kogyo Seiyaku Co., Ltd.) was changed from 0.10 g to 0.30 g. The latex particles had a particle size of 0.101 µm (CV: 10.8%).

Application Example 1

The following reagents and materials were used.
Reagents and Materials
Anti-D-dimer antibody
Antibody-immobilized latex preparation buffer: 20 mM Tris-HCl (pH: 8.0)
Blocking buffer: 20 mM Tris-HCl (pH: 8.0) including 2% BSA
Sample dilution buffer: 30 mM Tris-HCl (pH: 8.5) including 0.15% BSA
Preparation of D-Dimer Assay Reagent
The latex particles (latex particles of Examples 1 to 6 and Comparative Examples 1 to 3) were purified by centrifugation, and diluted to a concentration of 5% (w/v) using the antibody-immobilized latex preparation buffer to prepare a diluted latex liquid.

The anti-D-dimer antibody was diluted to a concentration of 1 mg/mL using the antibody-immobilized latex preparation buffer to prepare a diluted antibody solution.

One part by volume of the diluted antibody solution was added to one part by volume of the diluted latex liquid with stirring, followed by further stirring. Then, two parts by volume of the blocking buffer was further added, and the mixture was kept stirred. The mixture was collected, and adjusted to a concentration of 0.5% (w/v) to prepare an antibody-immobilized latex dispersion. A calibration curve was drawn using the antibody-immobilized latex dispersion and a D-dimer antigen standard solution.
System: 7170 Hitachi automatic analyzer (manufactured by Hitachi High-Technologies Corporation)
Wavelength: 570/800 nm, temperature: 37° C.
Test substance (D-dimer standard solution (0 to 58 μg/mL): 12 μL
First reagent (30 mM Tris-HCl (pH: 8.5) including 0.15% BSA): 100 μL
Second reagent (antibody-immobilized latex (0.5% (w/v)) dispersion): 100 μL
Number of photometric points: 18 to 34

Assay Example 1

An assay was performed according to the above method using the antibody-immobilized latex particles (0.5% (w/v)) dispersion prepared using the latex particles (latex particles of Examples 1 to 6 and Comparative Examples 1 to 3) sensitized with the anti-D-dimer antibody, and a calibration curve was drawn (see FIG. 1). A high-sensitivity assay could be implemented when using the latex particles of Examples 1 to 6. In contrast, a sensitivity lower than that achieved by the latex particles of Example 1 was obtained when using the latex particles of Comparative Examples 1 to 3.

Assay Example 2

Figure 2:
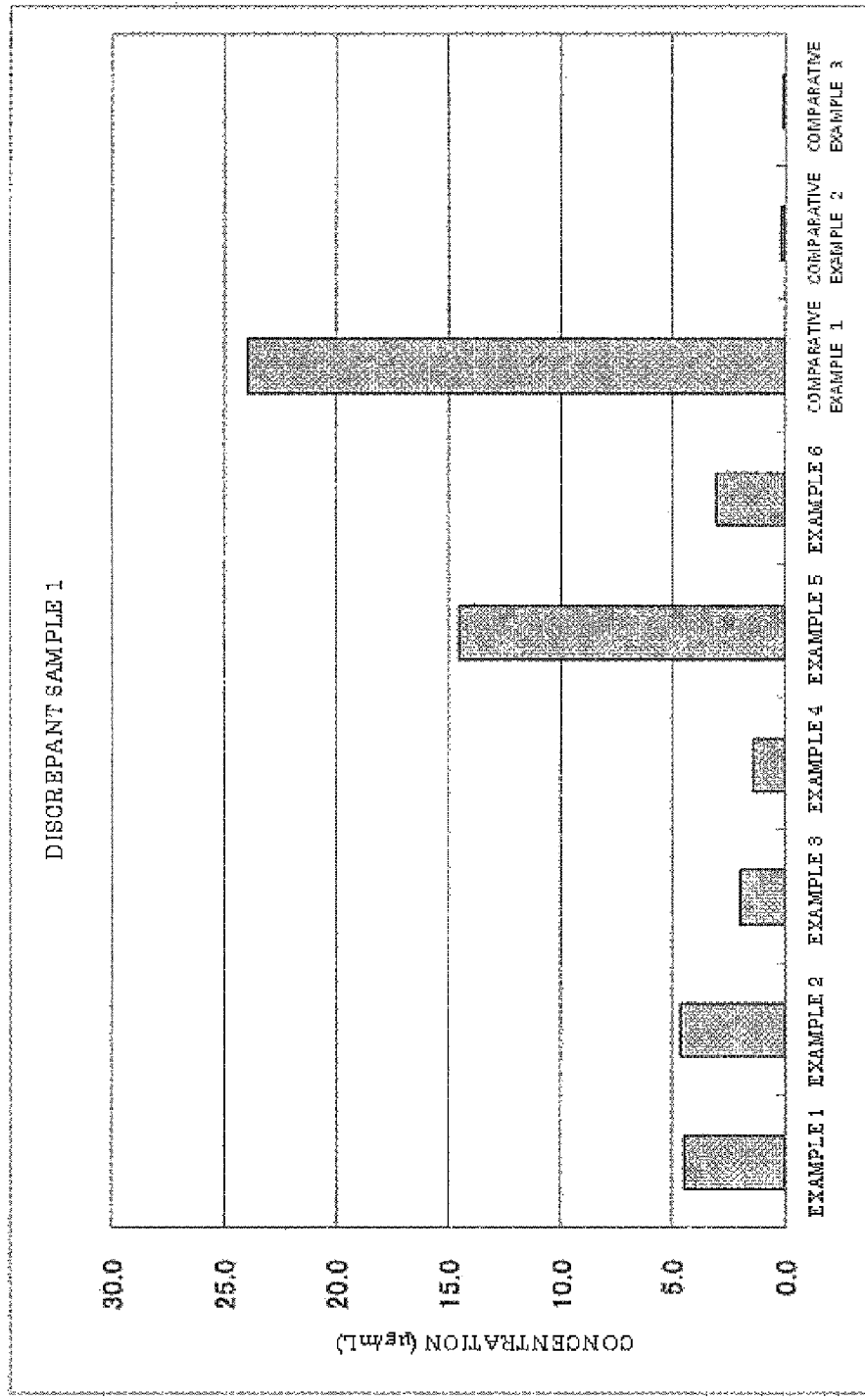
FIG. 2 illustrates a graph when an assay was performed on the D-dimer discrepant sample 1 (RF08FD1832) using the latex particles of Examples 1 to 6 and Comparative Examples 1 to 3 that were sensitized with the anti-D-dimer antibody, and the concentration was calculated based on the calibration curve (see FIG. 1).
Figure 3:
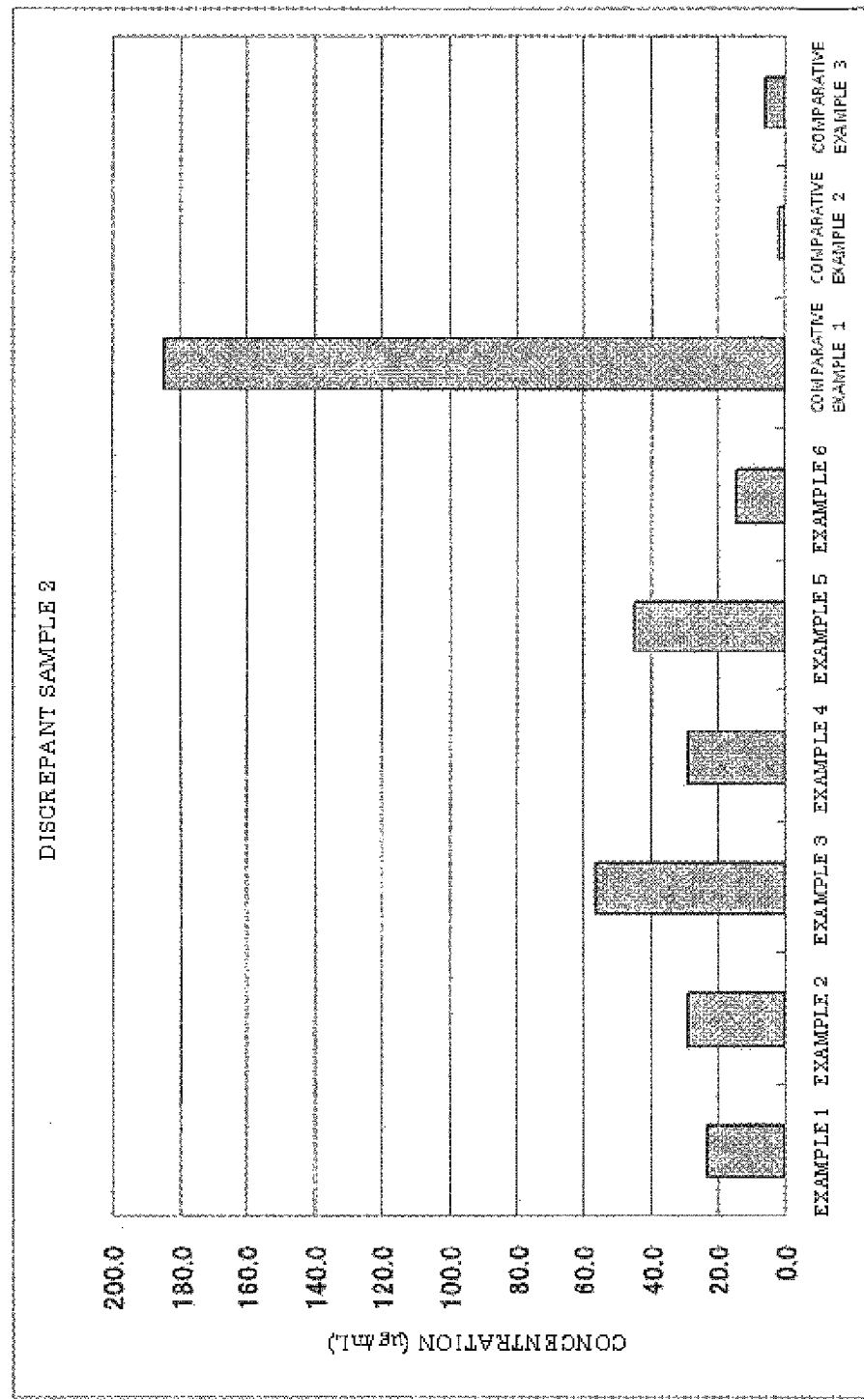
FIG. 3 illustrates a graph when an assay was performed on the D-dimer discrepant sample 2 (RF08FD1836) using the latex particles of Examples 1 to 6 and Comparative Examples 1 to 3 that were sensitized with the anti-D-dimer antibody, and the concentration was calculated based on the calibration curve (see FIG. 1).

An assay was performed according to the above method using the antibody-immobilized latex particles (0.5% (w/v)) dispersion prepared using the latex particles (latex particles of Examples 1 to 6 and Comparative Examples 1 to 3) sensitized with the anti-D-dimer antibody, and a D-dimer discrepant sample (two samples); and the concentration was calculated based on the calibration curve obtained in Assay Example 1. Note that the D-dimer discrepant sample here refers to a sample for which a non-specific agglutination reaction was observed using a known D-dimer immunoturbidimetric assay system. The results are illustrated in FIGS. 2 and 3.
When using the latex particles of Examples 1 to 6, a non-specific agglutination reaction of the discrepant sample could be highly suppressed as compared with the case of using the latex particles of Comparative Example 1 in which a nonionic surfactant was not used. When using the latex particles of Comparative Examples 2 to 3, a non-specific agglutination reaction of the discrepant sample could be highly suppressed as compared with the case of using the latex particles of Examples 1 to 6. However, since the sensitivity decreased significantly, it is considered that the antibody was not sufficiently adsorbed on the surface of the latex particles (i.e., the latex particles were not sufficiently sensitized).

Application Example 2

The following reagents and materials were used.
Reagents and Materials

See Application Example 1.
Preparation of D-Dimer Assay Reagent

An antibody-immobilized latex dispersion was prepared in the same manner as in Application Example 1, except that the latex particles obtained in Examples 7 to 9 and Comparative Examples 4 and 5 were used.

A calibration curve was drawn using the antibody-immobilized latex dispersion and a D-dimer antigen standard solution.
System: 7170 Hitachi automatic analyzer (manufactured by Hitachi High-Technologies Corporation)
Wavelength: 570/800 nm, temperature: 37° C.
Test substance (D-dimer standard solution (0 to 58 μg/mL): 12 μL
First reagent (30 mM Tris-HCl (pH: 8.5) including 0.15% BSA): 100 μL
Second reagent (antibody-immobilized latex (0.5% (w/v)) dispersion): 100 μL
Number of photometric points: 18 to 34

Assay Example 3

Figure 4:
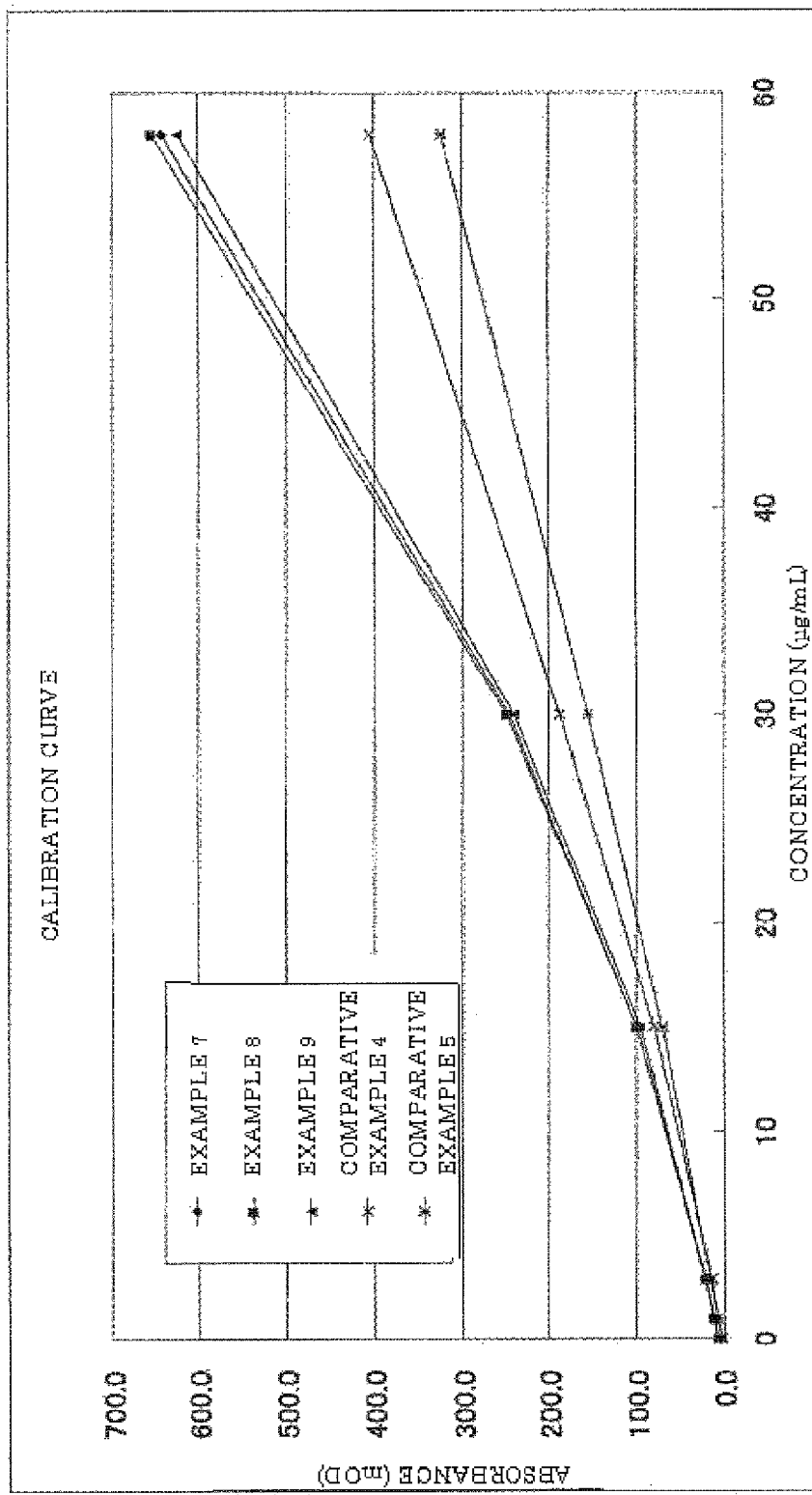
FIG. 4 illustrates a calibration curve drawn when an assay was performed on the standard D-dimer antigen using the latex particles of Examples 7 to 9 and Comparative Examples 4 and 5 that were sensitized with the anti-D-dimer antibody.

An assay was performed according to the above method using the antibody-immobilized latex (0.5% (w/v)) dispersion prepared using the latex particles (latex particles of Examples 7 to 9 and Comparative Examples 4 and 5) sensitized with the anti-D-dimer antibody, and a calibration curve was drawn (see FIG. 4). A high-sensitivity assay could be implemented when using the latex particles of Examples 7 to 9. In contrast, a sensitivity lower than that achieved by the latex particles of Examples 7 to 9 was obtained when using the latex particles of Comparative Examples 4 and 5.

Assay Example 4

An assay was performed according to the above method using the antibody-immobilized latex (0.5% (w/v)) dispersion prepared using the latex particles (latex particles of Examples 7 to 9 and Comparative Examples 4 and 5) sensitized with the anti-D-dimer antibody, and a D-dimer discrepant sample (two samples) (see Application Example 1), and the concentration was calculated based on the calibration curve obtained in Assay Example 3. The results are illustrated in FIGS. 5 and 6. When using the latex particles of Examples 7 to 9, a non-specific agglutination reaction of the discrepant sample could be highly suppressed as compared with the case of using the latex particles of Comparative Example 4 in which the nonionic surfactant was used at a low concentration. When using the latex particles of Comparative Example 5, a non-specific agglutination reaction of the discrepant sample could be highly suppressed as compared with the case of using the latex particles of Examples 7 to 9. However, since the sensitivity decreased significantly, it is considered that the antibody was not sufficiently adsorbed on the surface of the latex particles (i.e., the latex particles were not sufficiently sensitized).

INDUSTRIAL APPLICABILITY

The latex particles according to the invention may be used for an immunoassay that utilizes an antigen-antibody reaction (particularly latex immunoturbidimetry that utilizes latex particles). An arbitrary substance that specifically reacts with the detection target substance may be used as long as it is a physiologically active substance that is normally used as an immunoserological assay reagent (i.e., a reagent used for immunoagglutination and agglutination inhibition) or a biochemical assay reagent.

The invention claimed is:

1. Latex particles for a particle agglutination assay, wherein the latex particles which include a polymerizable monomer having a phenyl group, and a polymerizable monomer having a phenyl group and a sulfonate are formed by an emulsion polymerization performed in an aqueous medium including a nonionic surfactant at a concentration of 0.005 to 0.02 weight percent (wt %) based on the aqueous medium, wherein the latex particles have an average particle size of 0.005 to 1.0 μm, wherein the nonionic surfactant is a polyoxyethylene-polyoxypropylene block copolymer or a polyoxyalkylene alkyl ether, wherein the polyoxyethylene-polyoxypropylene block copolymer if used has a structure represented by a formula (I), and has a weight average molecular weight of 1000 to 15,000 and an oxyethylene content of 5 to 90%, $$HO(C_2H_4O)a\text{-}(C_3H_6O)b\text{-}(C_2H_4O)cH \qquad (I)$$

wherein a, b, and c are arbitrary integers, a+c being determined so that oxyethylene has an average degree of polymerization of 2 to 270, and b being determined so that oxypropylene has an average degree of polymerization of 15 to 40, provided that a+b+c is 17 to 300, wherein the polyoxyalkylene alkyl ether if used has a structure represented by a formula (II), and has an hydrophilic-lipophilic balance value of 5.0 to 19.3, $$R1O(AO)n\text{-}H \qquad (II)$$

wherein R1 is an alkyl group or an alkenyl group having 8 to 22 carbon atoms, AO is an oxyalkylene group, A is an alkyl group having 2 to 4 carbon atoms, and n is an integer from 2 to 15, n being the average number of moles of the oxyalkylene group represented by AO.

2. The latex particles according to claim 1, wherein the polyoxyethylene-polyoxypropylene block copolymer is selected from a group consisting of
(1) a polyoxyethylene-polyoxypropylene block copolymer having a weight average molecular weight of 1333 and an oxyethylene content of 10%,
(2) a polyoxyethylene-polyoxypropylene block copolymer having a weight average molecular weight of 2222 and an oxyethylene content of 10%,
(3) a polyoxyethylene-polyoxypropylene block copolymer having a weight average molecular weight of 8000 and an oxyethylene content of 85%, and
(4) a polyoxyethylene-polyoxypropylene block copolymer having a weight average molecular weight of 13,333 and an oxyethylene content of 85%.

3. The latex particles according to claim 1, wherein the polyoxyalkylene alkyl ether is selected from a group consisting of (1) polyoxyethylene tridecyl ether with a hydrophilic-lipophilic balance of 10.5, (2) polyoxyethylene lauryl ether with a hydrophilic-lipophilic balance of 9.5, and (3) polyoxyethylene 2-ethylhexyl ether with a hydrophilic-lipophilic balance of 14.6.

4. The latex particles according to claim 1, wherein the polymerizable monomer having a phenyl group is styrene, and a polymerizable monomer having a phenyl group and a sulfonate is sodium styrenesulfonate.

5. A particle agglutination assay reagent comprising the latex particles according to any one of claims 1, 2, 3, and 4.

6. A particle agglutination assay reagent comprising the latex particles according to any one of claims 1, 2, 3, and 4, the latex particles supporting an antigen or an antibody through physical adsorption.

7. A method of preparing the latex particles of any one of claims 1, 2, 3, and 4, the method comprising:
performing an emulsion polymerization with a polymerizable monomer having a phenyl group, and a polymerizable monomer having a phenyl group and a sulfonate in an aqueous medium including a nonionic surfactant at a concentration of 0.005 to 0.02 weight percent (wt %) based on the aqueous medium.

8. A method of preparing latex particles for an agglutination assay having an average particle size of 0.05 to 0.4 μm, said method comprising:
performing an emulsion polymerization with a polymerizable monomer having a phenyl group, and a polymerizable monomer having a phenyl group and a sulfonate in an aqueous medium including a nonionic surfactant at a concentration of 0.005 to 0.02 weight percent (wt %) based on the aqueous medium at a polymerization temperature of 60° C. to 85° C.,
wherein the nonionic surfactant is a polyoxyethylene-polyoxypropylene block copolymer or a polyoxyalkylene alkyl ether,
wherein the concentration of the latex particles is from 1 to 20% based on the aqueous medium,
wherein the polyoxyethylene-polyoxypropylene block copolymer if used has a structure represented by a formula (I), and has a weight average molecular weight of 1000 to 15,000 and an oxyethylene content of 5 to 90%, $$HO(C_2H_4O)a\text{-}(C_3H_6O)b\text{-}(C_2H_4O)cH \qquad (I)$$

wherein a, b, and c are arbitrary integers, a+c being determined so that oxyethylene has an average degree of polymerization of 2 to 270, and b being determined so that oxypropylene has an average degree of polymerization of 15 to 40, provided that a+b+c is 17 to 300,
wherein the polyoxyalkylene alkyl ether if used has a structure represented by a formula (II), and has an hydrophilic-lipophilic balance value of 5.0 to 19.3, $$R1O(AO)n\text{-}H \qquad (II)$$

wherein R1 is an alkyl group or an alkenyl group having 8 to 22 carbon atoms, AO is an oxyalkylene group, A is an alkyl group having 2 to 4 carbon atoms, and n is an integer from 2 to 15, n being the average number of moles of the oxyalkylene group represented by AO.

9. The method of preparing the latex particles according to claim 8, wherein the polymerizable monomer having a phenyl group is styrene, and a polymerizable monomer having a phenyl group and a sulfonate is sodium styrenesulfonate.

10. The method of preparing the latex particles according to claim 9, wherein the aqueous medium comprises water.

11. The method of preparing the latex particles according to claim 8, wherein the polyoxyalkylene alkyl ether is selected from a group consisting of (1) polyoxyethylene tridecyl ether with a hydrophilic-lipophilic balance of 10.5, (2) polyoxyethylene lauryl ether with a hydrophilic-lipophilic balance of 9.5, and (3) polyoxyethylene 2-ethylhexyl ether with a hydrophilic-lipophilic balance of 14.6.

* * * * *